United States Patent [19]

Armitage

[11] 4,305,115
[45] Dec. 8, 1981

[54] ELECTROSTATIC SHIELD

[75] Inventor: David Armitage, Bangor, Wales

[73] Assignee: Harry H. LeVeen, Charleston, S.C.

[21] Appl. No.: 20,357

[22] Filed: Mar. 14, 1979

[51] Int. Cl.³ .............................................. A61N 1/06
[52] U.S. Cl. ................... 361/437; 128/804; 336/84 C; 361/212
[58] Field of Search ............... 361/212, 437; 128/804; 174/35 R, 35 CE, 6 C; 336/84 R, 84 C, 87; 324/327–329; 335/301

[56] References Cited

U.S. PATENT DOCUMENTS

| | | | |
|---|---|---|---|
| 1,059,666 | 4/1913 | Fessenden | 336/87 X |
| 2,047,159 | 7/1936 | Wood et al. | 174/35 CE |
| 2,276,996 | 3/1942 | Milinowski | 128/804 |
| 3,662,757 | 5/1972 | Blackett | 128/416 |
| 4,006,748 | 2/1977 | Schulman | 128/419 P |
| 4,068,292 | 1/1978 | Berry et al. | 361/437 |
| 4,071,032 | 1/1978 | Schulman | 128/419 P |

FOREIGN PATENT DOCUMENTS

| | | | |
|---|---|---|---|
| 129022 | 2/1932 | Fed. Rep. of Germany | 336/84 C |
| 718637 | 3/1942 | Fed. Rep. of Germany | 128/804 |

*Primary Examiner*—Harry E. Moose, Jr.
*Attorney, Agent, or Firm*—Brooks, Haidt, Haffner & Delahunty

[57] ABSTRACT

An electrostatic shield for an induction coil of a shortwave diathermy unit in the form of radial conductors arranged in a plane with a common point at their center which is grounded. The shield is positioned perpendicularly to the axis of the induction coil between the patient and coil.

3 Claims, 3 Drawing Figures

ELECTROSTATIC SHIELD

This invention relates to short-wave diathermy apparatus for inducing local hyperthermia and in particular, provides an electrostatic shield for use with a diathermy induction coil to minimize damage to subcutaneous tissue.

Recently it has been found that short-wave diathermy (thermotherapy) can be utilized in the treatment of tumors (LeVeen U.S. Pat. No. 3,991,770). This treatment is predicated on the perception that blood flow in tumors is poor, and hence the tumor can be selectively heated to the point of destruction by utilizing relatively high-power, short-wave diathermy without damage to adjacent normal tissue, as the blood flow through the adjacent normal tissue cools at a faster rate than the slower blood flow through the tumor. In the treatment of tumors, the diathermy unit is generally of a higher power than used in conventional diathermy treatment and typically is on the order of up to 2 kilowatts.

When an induction coil is used as a means of inducing local hyperthermia in a patient, the peak radio frequency current passing through the coil is necessarily high in order to achieve adequate magnetic coupling between the coil and the patient. The high peak radio frequency current is usually achieved by tuning the coil by means of a parallel capacitance. Where a coil whose inductance is of the order of one $\mu$H, the peak radio frequency voltage across the coil is typically 3 to 10 kilovolts for an operating frequency of 27.12 MHz. Typically the coils are placed about 3 centimeters from the patient's surface giving a coil-to-patient capacitance of a few pF, resulting in a significant radio frequency current flowing in the subcutaneous tissue. The peak value of the current is given by the equation $$\hat{i} = \hat{V}/X_c = 2\pi f C \cdot \hat{V} \tag{1}$$

Substituting values of V=10 kV, C=2 pF and f=27.12 MHz in this equation gives a value for $\hat{i}$ of approximately 4 amperes, which corresponds to a local heating effect of approximately 5 watts/cm, assuming a subcutaneous (fatty) tissue conductivity of 0.06 mhos/meter and that the radio frequency current passes through an area of 50 square centimeters. Such a level of heating clearly causes excessive temperature elevation and severe damage to the cutaneous and subcutaneous tissue. The phenomenon is discussed in more detail in a paper by A. W. Guy et al, Proc. I.E.E.E. 62, 62-66 (No. 1 January, 1974).

This unwanted surface heating effect can be avoided by placing an electrostatic shield between the induction coil and the patient, which shield is preferably grounded.

It is an important object of this invention to provide an electrostatic shield suitable for use with high-powered short-wave diathermy equipment which will substantially reduce surface heating of the patient while providing minimal interference with the wanted induction heating deeply within the body.

It is another object of this invention to provide such an electrostatic shield which is capable of use with coils of varying diameter without changing the shield.

It is also an object of this invention to provide an electrostatic shield construction which minimizes the electrical length between pairs of points on the shield such that the electric potential in the plane of the shield can be more uniform and closer to ground potential.

These and other objects of this invention are obtained by the use of a disk shaped, flat electrostatic shield of nonmagnetic conductor material having a solid central portion from which a plurality of narrow radial strips extend outwardly to the perimeter of the disk. The radial strips are closely spaced together about the central portion and extend about the central portion. There are further provided additional annular bands of shorter narrow strips which are interleaved between the longer narrow strips and also extend to the perimeter of the disk such that as the spaces between the various radial strips emananting from the central portion grow larger they are filled in by the additional bands of interleaved radial strips. In this construction the interleaved radial strips and further annual bands spaced outwardly from the first radial bands of narrow strips are again interleaved as the spaces between the first two groups of bands become larger. This interleaving of additional bands of radial strips can be carried on as required by the diameter of the disk.

For a more complete understanding of the practical application of the principles of this invention, reference is made to the appended drawings in which.

Figure 1:
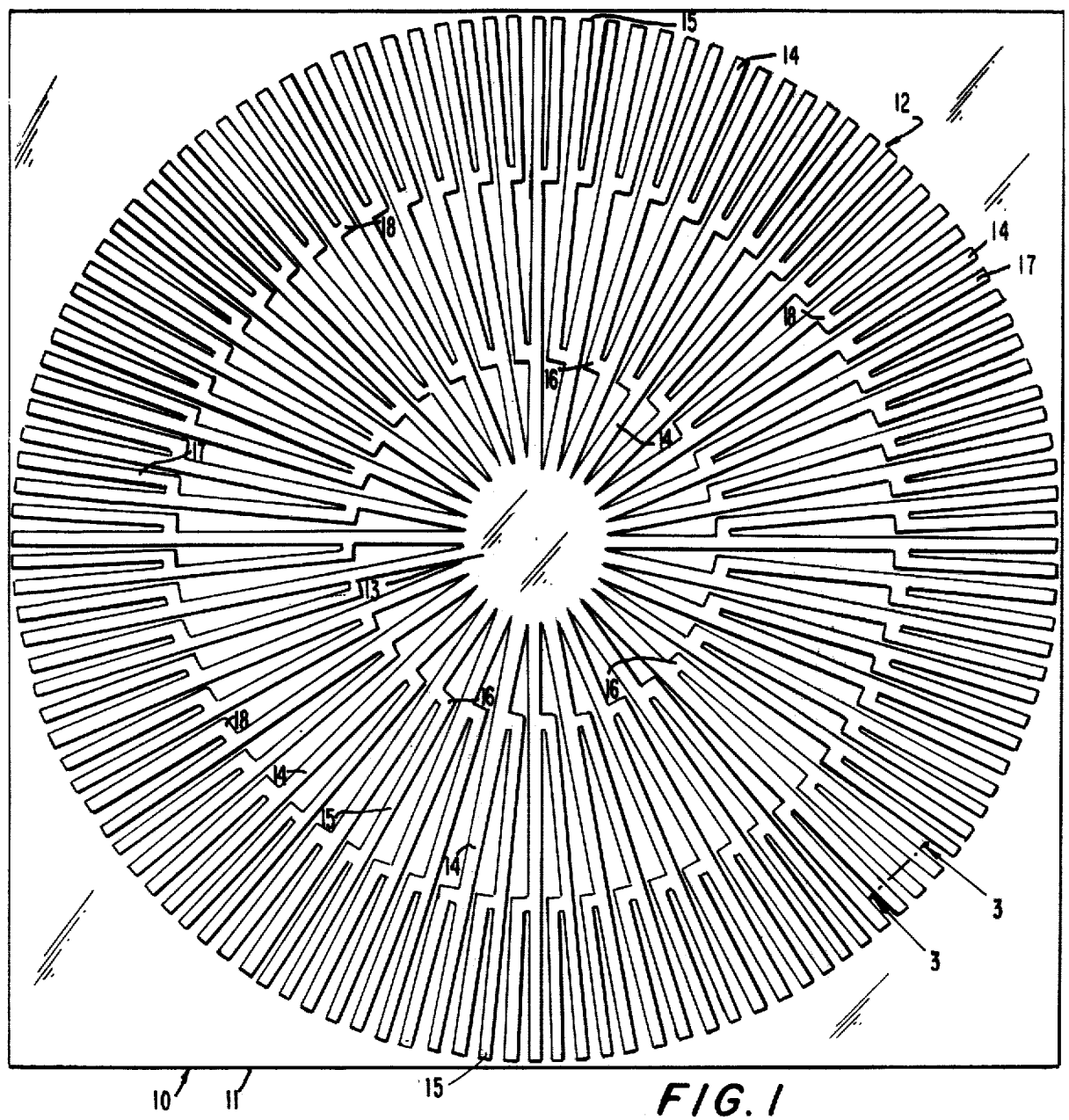
FIG. 1 is a plan view of an electrostatic shield in accordance with this invention.

Referring more particularly to FIG. 1, the reference numeral 10 designates an electrostatic shield in accordance with this invention. Shield 10, which is formed from a printed circuit blank, comprises a glass fiber reinforced, epoxy base panel 11 of generally flat, rectangular shape and a flat disk of silver foil 12 bonded to the face of panel 11. Panel 11 is approximately 21.3 centimeters by 20.6 centimeters by 1.52 millimeters, and disk 12 is approximately 0.076 millimeters in thickness with an overall diameter of 20.48 centimeters.

Disk 12 has a solid central portion of generally circular shape, having a diameter of 2.80 centimeters from which 32 narrow strips radiate to the perimeter of disk 12. Strips 14 are 2.54 millimeters wide and are spaced at equal arcuate intervals about central portion 13 of disk 12 and are 8.84 centimeters in length.

Disk 12 further includes an annular band of additional strips 15 which are also 32 in number and which are positioned radially with respect to disk 12, extending from an inner diameter of 6.83 centimeters, interleaved between strips 14 and spaced equally therefrom. Strips 15, which are also 2.54 millimeters in width, are 6.83 centimeters long and thus extend at their inner ends located 2.02 centimeters from central portion 13 to the perimeter of disk 12. Strips 15 are electrically interconnected with strips 14 at their inner ends as indicated by the reference numerals 16.

Disk 12 further includes yet another, outer, annular band of narrow strips 17, which are 64 in number, 2.54 millimeters in width and 3.34 centimeters long. Strips 17 are positioned radially in disk 12, interleaved between adjacent strips 14 and 15 and spaced equally between them. Strips 17 are located at their inner ends 5.51 centimeters from central portion 13 and extend to the perimeter of disk 12. Strips 17 are connected at their inner ends, as indicated by the reference numerals 18, alternately to strips 14 and 15.

Figure 2:
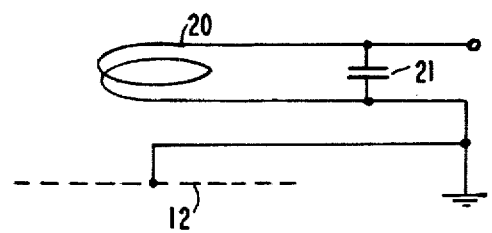
FIG. 2 is an electrical schematic diagram indicating the relative positioning of the shield and the induction coil.
Figure 3:
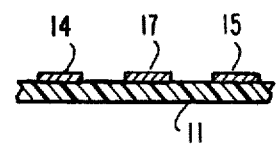
FIG. 3 is a fragmentary section taken at line 3—3 in FIG. 1.

As seen in FIG. 2, shield 10 is positioned such that disk 12 is associated with the induction coil 20 of a diathermy unit. Specifically, the shield should be centered on and perpendicular to the axis of the coil, such that solid portion 13 falls in the magnetically dead central area through coil 20 and is perpendicular to the axis of coil 20. Although a helix is indicated as coil 20 in FIG. 2, in practice it has been found preferable to use a pancake coil with one turn or two turns. It is best that disk 12 is approximately parallel to flat coil 20 and spaced preferably one or two centimeters from it. Coil 20, which is energized at a radio frequency typically of 13.56 MHz or 27.12 MHz, is tuned by means of a parallel capacitor 21. Central portion 13 of disk 12 is grounded to the same ground as coil 20. In use shield 10 is positioned between coil 20 and the patient and spaced from the patient 1 or 2 centimeters.

The stray capacitance between coil 20 and disk 12 has two effects. The radio frequency current flows in the electrostatic shield to ground instead of in the surface tissue of the patient. Secondly, the resonant frequency of the tuned circuit comprising coil 20 and its associated capacitor 21, is changed slightly. This is a constant effect which is compensated by adjusting the parallel tuning capacitor 21.

As a result of the presence of shield 10, any variation in the distance between the patient and the applicator does not alter the tuning of the resonant circuit. The Q of the resonant circuit is, however, still affected due to a variation in the magnetic coupling to the patient resulting either from variation in patient to applicator distance or from variation in the dielectric properties of the subcutaneous tissue.

What is claimed is:

1. An electrostatic shield which comprises a flat disk of non-magnetic, conductor material having a solid central portion and a plurality of narrow strips connected to, radiating outwardly from, and spaced closely together about said solid portion and extending spaced apart to and at the perimeter of said shield, and means for grounding said disk attached to said central portion thereof.

2. An electrostatic shield according to claim 1, in which said disk further comprises an annular band of a plurality of radial narrow strips interleaved between and spaced from adjacent pairs of said first named strips, each said second named strip at the inner end thereof being connected to one of said adjacent pair of first named strips and spaced outwardly from said central portion, and each said second named strip extending outwardly to the perimeter of said disk.

3. An electrostatic shield according to claim 2, which further comprises an annular band of radial narrow strips interleaved between adjacent pairs of said first and second named strips and spaced therefrom, each said third named strip being connected at the inner end thereof, outwardly of the inner ends of said second named strips alternately about said disk to one of said first and second named strips and each said third named strip extending outwardly to the perimeter of said disk.

* * * * *